United States Patent
Kozui

(10) Patent No.: US 12,264,140 B2
(45) Date of Patent: Apr. 1, 2025

(54) METHOD OF PRODUCING REFINED OILS AND/OR FATS, AND METHOD FOR PRODUCING TOCOPHEROLS

(71) Applicant: The Nisshin OilliO Group, Ltd., Tokyo (JP)

(72) Inventor: Hiroyuki Kozui, Yokohama (JP)

(73) Assignee: The Nisshin OilliO Group, Ltd., Tokyo (JP)

( * ) Notice: Subject to any disclaimer, the term of this patent is extended or adjusted under 35 U.S.C. 154(b) by 707 days.

(21) Appl. No.: 17/593,023

(22) PCT Filed: Dec. 20, 2019

(86) PCT No.: PCT/JP2019/050032
§ 371 (c)(1),
(2) Date: Sep. 3, 2021

(87) PCT Pub. No.: WO2020/194936
PCT Pub. Date: Oct. 1, 2020

(65) Prior Publication Data
US 2022/0177441 A1 Jun. 9, 2022

(30) Foreign Application Priority Data
Mar. 26, 2019 (JP) .................. 2019-058873

(51) Int. Cl.
*C07D 311/72* (2006.01)
*C11B 3/12* (2006.01)

(52) U.S. Cl.
CPC .............. *C07D 311/72* (2013.01); *C11B 3/12* (2013.01)

(58) Field of Classification Search
CPC .................................................. C07D 311/72
USPC ........................................................ 549/413
See application file for complete search history.

(56) References Cited

U.S. PATENT DOCUMENTS

| 5,190,618 A | 3/1993 | Top et al. |
| 7,531,678 B2 | 5/2009 | Choo et al. |

FOREIGN PATENT DOCUMENTS

| CN | 101445498 A | 6/2009 |
| EP | 3428255 A1 | 1/2019 |
| JP | H 02-009875 A | 1/1990 |
| WO | WO 2017/154638 A1 | 9/2017 |

OTHER PUBLICATIONS

Frank et al. "Influence of chemical refining process and oil type on bound 3-chloro-1, 2-propanediol contents in palm oil and rapeseed oil". LWT—Food Science and Technology, May 19, 2009, pp. 1751-1754.
Hiromori, Kousuke et al., Separation technology of vitamin E from rice bran oil, Oleoscience, 2017, vol. 17, No. 6, pp. 253-259.
Komori, Saburo et al., Semi-industrial molecular distillation of fats and oils, The Journal of the Society of Chemical Industry, Japan, vol. 55, vol. 7, 1952, pp. 466, 467.
Kitakawa, Naomi et al., Development of novel process for efficiently separating and purifying tocotrienols, Japan Journal of Food Engineering, 2016, vol. 17, No. 1, pp. 23-31.
Pudei et al. "3-MCPD and glycidyl esters can be mitigated in vegetable oils by use of short path distillation". European Journal of Lipid Science and Technology, 2016, vol. 118, May 22, 2015, 396-405.
Matthaeus, B. et al., "Mitigation of 3-MCPD and glycidyl esters within the production chain of vegetable oils especially palm oil". Lipid Technology, Jul. 10, 2013, vol. 25, No. 7, pp. 151-155.
Jiang, S. T. et al., Molecular distillation for recovering tocopherol and fatty acid methyl esters from rapeseed oil deodoriser distillate, Biosystems Engineering, Mar. 9, 2006, vol. 93, No. 4, pp. 383-391.
Posada, L. R. et al., Extraction of tocotrienols from palm fatty acid distillates using molecular distillation, Separation and Purification Technology, 2007, vol. 57, pp. 220-229.

*Primary Examiner* — Taofiq A Solola
(74) *Attorney, Agent, or Firm* — Knobbe, Martens, Olson & Bear, LLP

(57) ABSTRACT

A method of producing refined oils and/or fats whereby the content of, e.g., glycidol, can be reduced and reductions in the content of tocopherols can be inhibited, and a method for producing low-impurity tocopherols. The method includes a first distillation step of subjecting raw material oils and/or fats to thin film distillation under a first condition; a second distillation step of subjecting a first distillate fraction obtained after the first distillation step to thin film distillation under a second condition; a third distillation step of subjecting a second residual fraction obtained after the second distillation step to thin film distillation under a third condition; and a mixing step of obtaining a mixed oil by mixing a first residual fraction obtained after the first distillation step, with a third distillate fraction obtained after the third distillation step. The first, second, and third conditions include specified temperature conditions and pressure conditions.

17 Claims, 2 Drawing Sheets

METHOD OF PRODUCING REFINED OILS AND/OR FATS, AND METHOD FOR PRODUCING TOCOPHEROLS

This application is the U.S. National Phase under 35 U.S.C. § 371 of International Application PCT/JP2019/050032, filed Dec. 20, 2019, designating the U.S., and published in Japanese as WO 2020/194936 on Oct. 1, 2020, which claims priority to Japanese Patent Application No. 2019-058873, filed Mar. 26, 2019, the entire contents of which are incorporated herein by reference.

TECHNICAL FIELD

The present invention relates to a method of producing refined oils and/or fats and a method of producing tocopherols.

BACKGROUND ART

Some oils and/or fats contain trace components that are considered to affect physiological activity. Examples of such trace components include glycidol, 3-chloropropane-1,2-diol, and fatty acid esters thereof. Although it is suggested that such trace components might cause nutritional problems, they are not considered to have a direct effect on health if they are at levels where they are found in vegetable oils and other oils and/or fats that have been taken in through diet over many years, and no dietary reference intakes have been established for them. However, a need exists for safer oils and/or fats, and thus some methods are proposed for reducing such components from oils and/or fats.

Glycidol, 3-chloropropane-1,2-diol, and fatty acid esters thereof are known to be produced through deodorization processes and so on, and sometimes contained in a trace amount in common vegetable oils, such as deodorized rapeseed oil. Moreover, diglycerides are known as substances that can cause 3-chloropropane-1,2-diol and the like (see Non-Patent Document 1), which tend to be found in a relatively high concentration in diglyceride-rich oils and/or fats, in particular, refined palm-based oils and/or fats (e.g., palm oil, palm kernel oil). Therefore, for example, Patent Document 1 proposes a method of producing refined palm-based oils and/or fats, which includes thin film distillation under controlled temperature conditions to reduce the content of the components mentioned above.

Patent Document 1: PCT International Publication No. WO2017/154638

Non-Patent Document 1: LWT-Food Science and Technology 42 (2009) 1751-1754

DISCLOSURE OF THE INVENTION

Problems to be Solved by the Invention

Unfortunately, such a conventional method may also reduce the content of useful components in oils and/or fats even though it can reduce the content of glycidol, 3-chloropropane-1,2-diol, and fatty acid esters thereof. Such useful components include tocopherols.

It has also been difficult to extract only useful components from various components (glycidol, 3-chloropropane-1,2-diol, and fatty acid esters thereof, and useful components such as tocopherols) removed from oils and/or fats by the conventional method.

It is an object of the present invention, which has been made in light of the circumstances mentioned above, to provide refined oils and/or fats producing method capable of reducing the content of glycidol, 3-chloropropane-1,2-diol, and fatty acid esters thereof and capable of providing tocopherols at a less reduced concentration. It is another object of the present invention to provide a method of producing tocopherols with less impurities.

Means for Solving the Problems

The present inventors have completed the present invention based on findings that the problems can be solved using refined oils and/or fats producing method that includes carrying out thin film distillation multiple times and controlling temperature conditions for each time of thin film distillation. Specifically, the present invention provides the following.

(1) A method of producing refined oils and/or fats, including:
a first distillation step that includes subjecting raw material oils and/or fats to thin film distillation under a first condition;
a second distillation step that includes subjecting a first distillate fraction obtained after the first distillation step to thin film distillation under a second condition;
a third distillation step that includes subjecting a second residual fraction obtained after the second distillation step to thin film distillation under a third condition; and
a mixing step that includes mixing a first residual fraction obtained after the first distillation step and a third distillate fraction obtained after the third distillation step to obtain a mixed oil,
the first condition including a temperature of 250° C. or more and 290° C. or less and a degree of vacuum of 0.1 Pa or less, the second condition and the third condition each including a temperature lower than that in the first condition and a degree of vacuum of 0.1 Pa or less,
the temperature in the second condition being 5° C. or more and 15° C. or less lower than that in the third condition.

(2) A method of producing refined oils and/or fats, including:
a first distillation step that includes subjecting raw material oils and/or fats to thin film distillation under a first condition;
a third distillation step that includes subjecting a first distillate fraction obtained after the first distillation step to thin film distillation under a third condition;
a second distillation step that includes subjecting a third distillate fraction obtained after the third distillation step to thin film distillation under a second condition; and
a mixing step that includes mixing a first residual fraction obtained after the first distillation step and a second residual fraction obtained after the second distillation step to obtain a mixed oil,
the first condition including a temperature of 250° C. or more and 290° C. or less and a degree of vacuum of 0.1 Pa or less, the second condition and the third condition each including a temperature lower than that in the first condition and a degree of vacuum of 0.1 Pa or less, the temperature in the second condition being 5° C. or more and 15° C. or less lower than that in the third condition.

(3) The method according to aspect (1) or (2), wherein the temperature in the second condition is 175° C. or more and 185° C. or less.

(4) The method according to any one of aspects (1) to (3), wherein the temperature in the third condition is 185° C. or more and 195° C. or less.

(5) The method according to any one of aspects (1) to (4), wherein the raw material oils and/or fats are an oils and/or fats having undergone at least a deodorization step.

(6) The method according to any one of aspects (1) to (5), wherein the raw material oils and/or fats are a palm-based oils and/or fats.

(7) The method according to any one of aspects (1) to (6), wherein the thin film distillation is short-path distillation.

(8) A method of producing tocopherols, including:
a first distillation step that includes subjecting raw material oils and/or fats to thin film distillation under a first condition;
a second distillation step that includes subjecting a first distillate fraction obtained after the first distillation step to thin film distillation under a second condition;
a third distillation step that includes subjecting a second residual fraction obtained after the second distillation step to thin film distillation under a third condition; and
a collecting step that includes collecting a third distillate fraction obtained after the third distillation step,
the first condition including a temperature of 250° C. or more and 290° C. or less and a degree of vacuum of 0.1 Pa or less,
the second condition and the third condition each including a temperature lower than that in the first condition and a degree of vacuum of 0.1 Pa or less,
the temperature in the second condition being 5° C. or more and 15° C. or less lower than that in the third condition.

(9) A method of producing tocopherols, including:
a first distillation step that includes subjecting raw material oils and/or fats to thin film distillation under a first condition;
a third distillation step that includes subjecting a first distillate fraction obtained after the first distillation step to thin film distillation under a third condition;
a second distillation step that includes subjecting a third distillate fraction obtained after the third distillation step to thin film distillation under a second condition; and
a collecting step that includes collecting a second residual fraction obtained after the second distillation step,
the first condition including a temperature of 250° C. or more and 290° C. or less and a degree of vacuum of 0.1 Pa or less, the second condition and the third condition each including a temperature lower than that in the first condition and a degree of vacuum of 0.1 Pa or less,
the temperature in the second condition being 5° C. or more and 15° C. or less lower than that in the third condition.

Effects of the Invention

The present invention provides refined oils and/or fats producing method capable of reducing the content of glycidol, 3-chloropropane-1,2-diol, and fatty acid esters thereof and capable of providing tocopherols at a less reduced concentration, and provides a method of producing tocopherols with less impurities.

PREFERRED MODE FOR CARRYING OUT THE INVENTION

Figure 1:
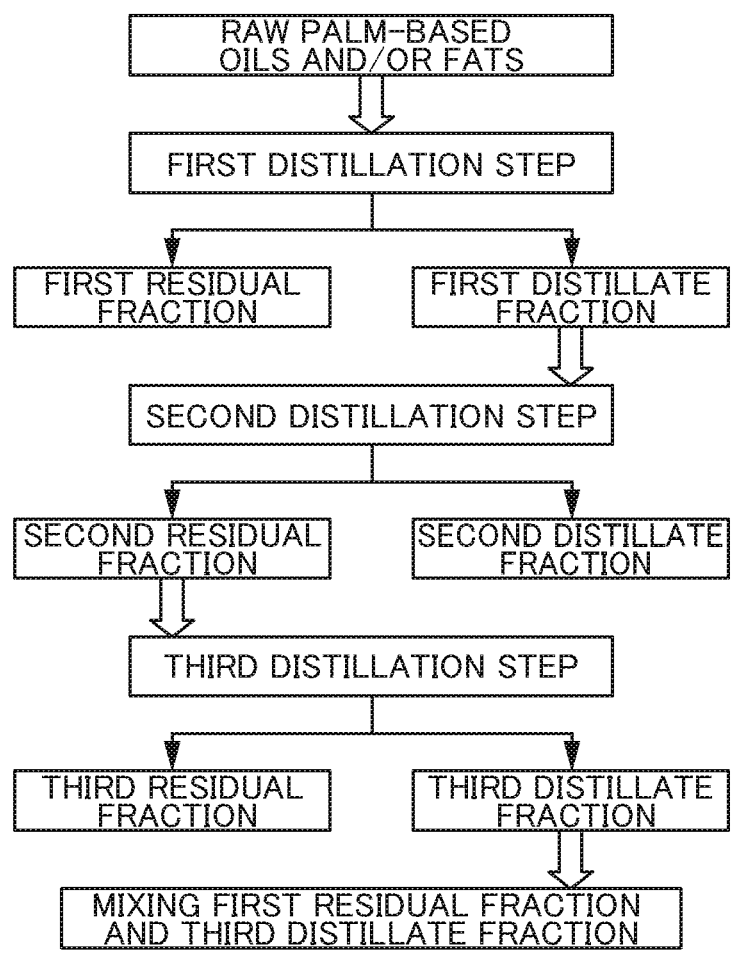
FIG. 1 is a diagram showing the outline of a production method in a first mode according the present invention.

Hereinafter, embodiments of the present invention will be described, which are not intended to limit the present invention.

<Method of Producing Refined Oils and/or Fats>

The method of producing refined oils and/or fats according to the present invention (hereinafter also referred to as "the production method of the present invention") includes carrying out thin film distillation multiple times. As used herein, the term "thin film distillation" refers to a process that includes forming, into a thin film, the material to be treated; and heating the thin film under reduced pressure for evaporation. A distillate fraction and a residual fraction are obtained from the material by such a process. The term "distillate fraction" refers to a component evaporated and separated from the material, and the term "residual fraction" refers to a component remaining after the separation of the distillate fraction from the material.

As a result of studies, the present inventors have found that, when raw material oils and/or fats are subjected to thin film distillation at a high temperature (e.g., 250° C. or more and 290° C. or less), the resulting residual fraction has a reduced content of glycidol, 3-chloropropane-1,2-diol (hereinafter also referred to as "3-MCPD"), and fatty acid esters thereof and that such a residual fraction provides useful refined oils and/or fats. On the other hand, it has been found that tocopherols, which are useful components, are separated from the refined oils and/or fats (residual fraction) into the distillate fraction, so that the content of tocopherols is significantly reduced. As used herein, the term "tocopherols" is a generic term which is intended to include tocopherol isomers (α-tocopherol, β-tocopherol, γ-tocopherol, and δ-tocopherol) and tocotrienol isomers (α-tocotrienol, β-tocotrienol, γ-tocotrienol, and δ-tocotrienol).

Thus, the present inventors have conducted intensive studies, and as a result, have found that, after the high-temperature thin film distillation of the raw material oils and/or fats, the resulting distillate fraction should be further subjected to thin film distillation under a different temperature condition, and the resulting component should be mixed with the refined oils and/or fats (residual fraction), so that refined oils and/or fats are obtained having a reduced content of glycidol and the like and containing tocopherols at a less reduced concentration.

Specifically, as a result of studies, the present inventors have found that glycidol, 3-MCPD, and fatty acid esters thereof, and tocopherols can be separated using thin film distillation steps under different temperature conditions. More specifically, glycidol, 3-MCPD, and fatty acid esters thereof, and tocopherols can be separated from oils and/or fats by thin film distillation at high temperature (under the first temperature condition described later). Glycidol and fatty acid esters thereof can be separated from oils and/or fats by thin film distillation at low temperature (under the second temperature condition described later). 3-MCPD and fatty acid esters thereof can be separated from oils and/or fats by thin film distillation at middle temperature (the third temperature condition described later). The production method of the present invention takes advantage of such a relationship and includes carrying out thin film distillation steps under different temperature conditions in a stepwise manner.

Figure 2:
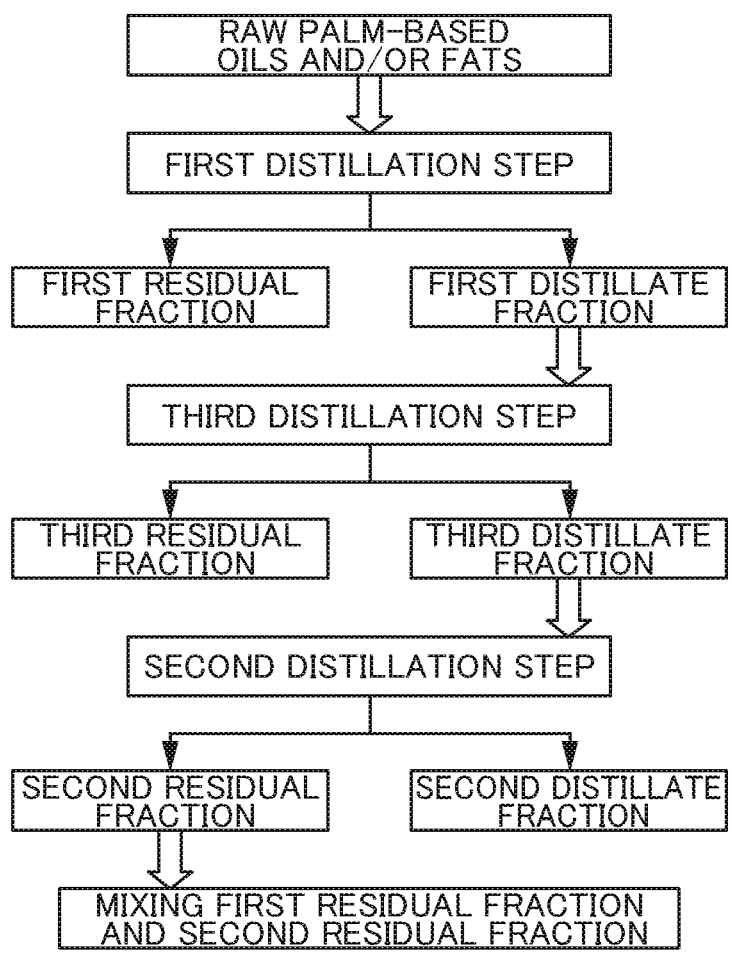
FIG. 2 is a diagram showing the outline of a production method in a second mode according to the present invention.

The outline of the production method of the present invention is shown in FIGS. 1 and 2. Hereinafter, the thin film distillation, the raw material oils and/or fats, and other features in the present invention will be described in detail.

(Raw Material Oils and/or Fats)

As used herein, the term "raw material oils and/or fats" refers to any oils and/or fats that contains tocopherols and is to be subjected to the production method of the present invention.

Examples of the raw material oils and/or fats include the following oils and/or fats containing tocopherols: vegetable oils; oils and/or fats synthesized from glycerin and fatty acids, and oils and/or fats obtained by fractionation of such synthesized oils and/or fats; transesterified oils; and hydrogenated oils. These oils and/or fats may be used alone, or a mixture of two or more of these oils and/or fats may be used.

Examples of the vegetable oils include palm-based oil, soybean oil, rapeseed oil, high-oleic rapeseed oil, sunflower oil, high-oleic sunflower oil, olive oil, safflower oil, high-oleic safflower oil, corn oil, cottonseed oil, rice oil, sesame oil, perilla oil, linseed oil, peanut oil, grapeseed oil, beef tallow, milk fat, fish oil, and coconut oil.

Examples of the oils and/or fats synthesized from glycerin and fatty acids include medium-chain triglycerides (MCTs).

Examples of the fractionated oils include fractionated oils made from palm oil, palm kernel oil, or coconut oil as a raw material.

Examples of the transesterified oils include oils produced by transesterification of palm-based oil with other oils and/or fats; and oils produced by transesterification of middle-chain fatty acid oil (MCT) with vegetable oils.

Examples of the hydrogenated oils include oils produced by hydrogenation of animal or vegetable oils or fractionated animal or vegetable oils; and oils produced by hydrogenation of transesterified oils.

To easily bring about the advantageous effects of the present invention, the raw material oils and/or fats preferably has a relatively high content of diglyceride or 3-MCPD. Examples of such oils and/or fats include palm-based oil, rice oil, and transesterified oils.

Examples of the palm-based oil include oils and/or fats derived from palm. Specific examples of the palm-based oil include palm oil, palm kernel oil, fractionated palm oil, fractionated palm kernel oil, hydrogenated palm oil, hydrogenated palm kernel oil, hydrogenated fractionated palm oil, hydrogenated fractionated palm kernel oil, and oils produced by transesterification of these oils. Examples of the fractionated palm oil include super olein, palm olein, palm mid fraction, and palm stearin. Examples of fractionated palm kernel oil include palm kernel olein and palm kernel stearin.

While the palm-based oil may have any properties, they preferably have an iodine value of 65 or less and more preferably less than 58 so that they can have a low content of unsaturated fatty acids and be less likely to produce trans fatty acids and highly stable against oxidation.

The raw material oils and/or fats may be any type, such as unrefined oils and/or fats or oils and/or fats having undergone refining steps other than thin film distillation (e.g., degumming, deacidification, water washing, decolorization, deodorization, fractionation). The oils and/or fats refining method may be, but not limited to, chemical refining or physical refining. The chemical refining may include subjecting raw oil, which is obtained through expression and extraction of a plant product as a raw material, to refining by degumming, alkali deacidification, decolorization, dewaxing, and deodorization to obtain refined oils and/or fats. The physical refining may include subjecting raw oil to refining by degumming, deacidification without using alkali, such as distillation, decolorization, and deodorization to obtain refined oils and/or fats. In this regard, oils and/or fats having undergone degumming, decolorization, and deodorization is called refined bleached deodorized oil (RBD oil).

The raw material oils and/or fats are preferably oils and/or fats having a high content of glycidol, 3-MCPD, and fatty acid esters thereof, so that an advantageous effect of the present invention, a reduction in the content of glycidol, 3-MCPD, and fatty acid esters thereof, can be easily brought about. Such oils and/or fats may be oils and/or fats having undergone deodorization (preferably deodorization at 200 to 280° C.). The raw material oils and/or fats are more preferably an RBD oil.

The raw material oils and/or fats may have undergone any step when tocopherols should be obtained with high purity.

The raw material oils and/or fats contain glycerides as main components and tocopherols. The raw material oils and/or fats may contain other components, such as plant sterols, lecithin, antioxidant components, and dye components.

(First Distillation Step)

The first distillation step includes subjecting the raw material oils and/or fats to thin film distillation under a first condition. The main objective of the first distillation step is to separate glycidol, 3-MCPD, fatty acid esters thereof, and tocopherols from the raw material oils and/or fats.

The first condition includes a temperature of 250° C. or more and 290° C. or less. The treatment of the raw material oils and/or fats at such a high temperature allows separation of glycidol, 3-MCPD, fatty acid esters thereof, and tocopherols from the raw material oils and/or fats, so that a first residual fraction and a first distillate fraction are obtained. The first residual fraction mainly includes oils and/or fats (triglycerides) and is preferably composed of oils and/or fats (triglycerides). The first distillate fraction includes glycidol, 3-MCPD, fatty acid esters thereof, and tocopherols.

In the first condition, the temperature preferably has a lower limit of 265° C. and more preferably a lower limit of 270° C. In the first condition, the temperature preferably has an upper limit of 285° C. and more preferably an upper limit of 280° C.

In the first condition, the temperature is preferably in the range of 250° C. or more and 285° C. or less, the range of 250° C. or more and 280° C. or less, the range of 265° C. or more and 290° C. or less, the range of 265° C. or more and 285° C. or less, the range of 265° C. or more and 280° C. or less, the range of 270° C. or more and 290° C. or less, the range of 270° C. or more and 285° C. or less, or the range of 270° C. or more and 280° C. or less.

A relatively high temperature in the first condition makes it easier to separate glycidol, 3-MCPD, and fatty acid esters thereof from the raw material oils and/or fats.

It should be noted hereinafter that, in the present invention, the temperature condition for the thin film distillation corresponds to the temperature of the evaporating surface of a thin film evaporator. Specifically, in the present invention, the expression "the temperature condition for thin film distillation is 250° C. or more and 290° C. or less" means that the evaporating surface of a thin film evaporator has a temperature of 250° C. or more and 290° C. or less. For example, when the thin film distillation is carried out using a short-path evaporator, the temperature condition for the thin film distillation corresponds to the temperature of the evaporator.

The first condition includes a degree of vacuum of 0.1 Pa or less. In the first condition, the degree of vacuum is preferably close to 0 (zero) Pa so that a sufficient mean free path can be obtained in the evaporator and that high-boiling-point materials or the like can be easily removed. In the first condition, the degree of vacuum is preferably 0.05 Pa or less and more preferably 0.01 Pa or less.

It should be noted that, in the present invention, the "degree of vacuum" is expressed in terms of absolute pressure. The degree of vacuum indicates how close to the ideal vacuum state (absolute vacuum) it is when the absolute vacuum is expressed as zero.

The first distillation step is followed by a second distillation step and a third distillation step, in which each step includes carrying out thin film distillation under a predetermined condition. The second distillation step and the third distillation step may be performed in any order. Hereinafter, a mode in which the first, second, and third distillation steps are performed in order of first, second, and third is referred to as a "first mode", and a mode in which the distillation steps are performed in order of first, third, and second is referred to as a "second mode". FIG. 1 shows the outline of the first mode. FIG. 2 shows the outline of the second mode.

(Second Distillation Step in First Mode)

In the first mode, the second distillation step includes subjecting the first distillate fraction obtained after the first distillation step to thin film distillation under a second condition. The main objective of the second distillation step is to separate glycidol and fatty acid esters thereof from the first distillate fraction.

In the first mode, the second condition includes a temperature that is lower than that in the first condition and is 5° C. or more and 15° C. or less lower than that in the third condition (described later). The temperature in the second condition is preferably 8° C. or more and 12° C. or less lower than that in the third condition. The treatment of the first distillate fraction at such a low temperature allows separation of fatty acids, glycidol, and fatty acid esters thereof into a distillate fraction, so that a second residual fraction and a second distillate fraction are obtained. The second residual fraction mainly includes tocopherols, 3-MCPD, and fatty acid esters thereof. The second distillate fraction mainly includes fatty acids, glycidol, and fatty acid esters thereof.

In the first mode, the temperature in the second condition preferably has a lower limit of 175° C. and more preferably a lower limit of 178° C. The temperature in the second condition preferably has an upper limit of 185° C., more preferably an upper limit of 184° C., and even more preferably an upper limit of 183° C.

In the first mode, the temperature in the second condition is preferably in the range of 175° C. or more and 185° C. or less, the range of 175° C. or more and 184° C. or less, the range of 175° C. or more and 183° C. or less, the range of 178° C. or more and 185° C. or less, the range of 178° C. or more and 184° C. or less, or the range of 178° C. or more and 183° C. or less. In order to more reliably transfer tocopherols into the second residual fraction, the temperature in the second condition is more preferably 178° C. or more and 183° C. or less.

In the first mode, the difference between the temperatures in the second and third conditions preferably has a lower limit of 8° C. and more preferably a lower limit of 10° C. The difference preferably has an upper limit of 14° C. and more preferably an upper limit of 12° C.

In the first mode, the second condition includes a degree of vacuum of 0.1 Pa or less. In the second condition, the degree of vacuum is preferably close to 0 (zero) Pa so that a sufficient mean free path can be obtained in the evaporator and that high-boiling-point materials or the like can be easily removed. In the second condition, the degree of vacuum is preferably 0.05 Pa or less and more preferably 0.01 Pa or less.

(Third Distillation Step in First Mode)

In the first mode, the third distillation step includes subjecting the second residual fraction obtained after the second distillation step to thin film distillation under a third condition. The main objective of the third distillation step is to separate 3-MCPD and fatty acid esters thereof from the second residual fraction.

In the first mode, the third condition includes a temperature that is lower than that in the first condition and is 5° C. or more and 15° C. or less higher than that in the second condition. The temperature in the third condition is preferably 8° C. or more and 12° C. or less higher than that in the second condition. The treatment of the second residual fraction at such a middle temperature allows separation of 3-MCPD and fatty acid esters thereof into a residual fraction, so that a third residual fraction and a third distillate fraction are obtained. The third residual fraction mainly includes 3-MCPD and fatty acid esters thereof. The third distillate fraction mainly includes tocopherols.

In the first mode, the temperature in the third condition preferably has a lower limit of 185° C., more preferably a lower limit of 186° C., and even more preferably a lower limit of 188° C. The temperature in the third condition preferably has an upper limit of 195° C. and more preferably an upper limit of 193° C.

In the first mode, the temperature in the third condition is preferably in the range of 185° C. or more and 195° C. or less, the range of 185° C. or more and 193° C. or less, the range of 184° C. or more and 195° C. or less, the range of 184° C. or more and 193° C. or less, the range of 188° C. or more and 195° C. or less, or the range of 188° C. or more and 193° C. or less. In order to more reliably transfer tocopherols into the third residual fraction, the temperature in the third condition is more preferably 188° C. or more and 193° C. or less.

In the first mode, the third condition includes a degree of vacuum of 0.1 Pa or less. In the third condition, the degree of vacuum is preferably close to 0 (zero) Pa so that a sufficient mean free path can be obtained in the evaporator and that high-boiling-point materials or the like can be easily removed. In the third condition, the degree of vacuum is preferably 0.05 Pa or less and more preferably 0.01 Pa or less.

(Third Distillation Step in Second Mode)

In the second mode, the third distillation step includes subjecting the first distillate fraction obtained after the first distillation step to thin film distillation under a third condition. The main objective of the third distillation step is to separate 3-MCPD and fatty acid esters thereof from the first distillate fraction.

In the second mode, the third condition includes a temperature that is lower than that in the first condition and is 5° C. or more and 15° C. or less higher than that in the second condition. The temperature in the third condition is preferably 8° C. or more and 12° C. or less higher than that in the second condition. The treatment of the first distillate fraction at such a middle temperature allows separation of 3-MCPD and fatty acid esters thereof into a residual fraction, so that a third residual fraction and a third distillate fraction are obtained. The third residual fraction mainly includes 3-MCPD and fatty acid esters thereof. The third distillate fraction mainly includes fatty acids, glycidol, fatty acid esters thereof, and tocopherols.

In the second mode, the temperature in the third condition preferably has a lower limit of 185° C., more preferably a lower limit of 186° C., and even more preferably a lower limit of 188° C. The temperature in the third condition preferably has an upper limit of 195° C. and more preferably an upper limit of 193° C.

In the second mode, the temperature in the third condition is preferably in the range of 185° C. or more and 195° C. or less, the range of 185° C. or more and 193° C. or less, the range of 184° C. or more and 195° C. or less, the range of 184° C. or more and 193° C. or less, the range of 188° C. or more and 195° C. or less, or the range of 188° C. or more and 193° C. or less. In order to more reliably transfer tocopherols into the third residual fraction, the temperature in the third condition is more preferably 188° C. or more and 193° C. or less.

In the second mode, the third condition includes a degree of vacuum of 0.1 Pa or less. In the third condition, the degree of vacuum is preferably close to 0 (zero) Pa so that a sufficient mean free path can be obtained in the evaporator and that high-boiling-point materials or the like can be easily removed. In the third condition, the degree of vacuum is preferably 0.05 Pa or less and more preferably 0.01 Pa or less.

(Second Distillation Step in Second Mode)

In the second mode, the second distillation step includes subjecting the third distillate fraction obtained after the third distillation step to thin film distillation under a second condition. The main objective of the second distillation step is to separate glycidol and fatty acid esters thereof from the third distillate fraction.

In the second mode, the second condition includes a temperature that is lower than that in the first condition and is 5° C. or more and 15° C. or less lower than that in the third condition. The temperature in the second condition is preferably 8° C. or more and 12° C. or less lower than that in the third condition. The treatment of the third distillate fraction at such a low temperature allows separation of glycidol and fatty acid esters thereof into a distillate fraction, so that a second residual fraction and a second distillate fraction are obtained. The second residual fraction mainly includes tocopherols. The second distillate fraction mainly includes fatty acids, glycidol, and fatty acid esters thereof.

In the second mode, the temperature in the second condition preferably has a lower limit of 175° C. and more preferably a lower limit of 178° C. The temperature in the second condition preferably has an upper limit of 185° C., more preferably an upper limit of 184° C., and even more preferably an upper limit of 183° C.

In the second mode, the temperature in the second condition is preferably in the range of 175° C. or more and 185° C. or less, the range of 175° C. or more and 184° C. or less, the range of 175° C. or more and 183° C. or less, the range of 178° C. or more and 185° C. or less, the range of 178° C. or more and 184° C. or less, or the range of 178° C. or more and 183° C. or less. In order to more reliably transfer tocopherols into the second residual fraction, the temperature in the second condition is more preferably 178° C. or more and 183° C. or less.

In the second mode, the difference between the temperatures in the second and third conditions preferably has a lower limit of 8° C. and more preferably a lower limit of 10° C. The difference preferably has an upper limit of 14° C. and more preferably an upper limit of 12° C.

In the second mode, the second condition includes a degree of vacuum of 0.1 Pa or less. In the second condition, the degree of vacuum is preferably close to 0 (zero) Pa so that a sufficient mean free path can be obtained in the evaporator and that high-boiling-point materials or the like can be easily removed. In the second condition, the degree of vacuum is preferably 0.05 Pa or less and more preferably 0.01 Pa or less.

(Other Conditions for Distillation Steps)

In either of the first and second modes, each distillation step may further include any other conditions as long as the requirements described above are satisfied. Other exemplary conditions will be shown below, which may be employed in the present invention and shared by the respective distillation steps.

While the method may include any other refining step (such as decolorization) between the distillation steps, it preferably includes no refining step between the distillation steps (in other words, the distillation steps are preferably carried out continuously).

The duration of the thin film distillation means the time period for which the material being treated exists on the evaporating surface of the thin film evaporator. The duration of the thin film distillation is preferably, but not limited to, 1 second or more and more preferably 3 seconds or more for sufficient distillation. To reduce a thermal effect on the material being treated, the duration of the thin film distillation is preferably 5 minutes or less, more preferably 3 minutes or less, even more preferably 1 minute or less, and most preferably 30 seconds or less.

Examples of the type of thin film distillation include molecular distillation, which is carried out under high vacuum (0.1 Pa or less) using a condenser located within a distance shorter than the mean free path of the evaporated molecules; and short-path distillation, which is carried out using a condenser located at a distance equal to or around the mean free path of the evaporated molecules. In the present invention, short-path distillation is preferably carried out, which can provide high distillation efficiency.

The thin film distillation may be carried out using any thin film evaporator, such as a falling liquid film evaporator, a centrifugal evaporator, a rising liquid film evaporator, or a wiped film evaporator. A wiped film evaporator is preferred because of advantages such as a short time of retention of the material being treated in it and less thermal effect on the material being treated. The evaporating surface of the thin film evaporator may be made of any material, such as glass or stainless steel.

(Mixing Step)

In the first mode, the mixing step includes mixing the first residual fraction and the third distillate fraction to obtain a mixed oil. In the second mode, the mixing step includes mixing the first residual fraction and the second residual fraction to obtain a mixed oil. In the present invention, such a mixed oil is called a "refined oils and/or fats".

In the first mode, the first residual fraction mainly includes oils and/or fats (triglycerides), and the third distillate fraction mainly includes tocopherols. In the second mode, the first residual fraction mainly includes oils and/or fats (triglycerides), and the second residual fraction mainly includes tocopherols. In each mode, therefore, the mixing of the fractions provides refined oils and/or fats having a reduced content of glycidol, 3-chloropropane-1,2-diol, and fatty acid esters thereof and containing tocopherols at a less reduced concentration.

The refined oils and/or fats may be distributed without any modification or may be subjected to a further refining step. For example, the refined oils and/or fats may be subjected to a deodorization step (preferably, a step performed at a relatively low deodorization temperature of 200° C. or less).

Any known appropriate materials (e.g., an antioxidant, a dye, an emulsifier) may be added to the refined oils and/or fats.

<Determination of the Content of Glycidol, 3-Chloropropane-1,2-Diol, and Fatty Acid Esters Thereof in Refined Oils and/or Fats>

The production method of the present invention provides refined oils and/or fats with a reduced content of glycidol, 3-chloropropane-1,2-diol, and fatty acid esters thereof.

The production method of the present invention can also provide refined oils and/or fats with a reduced acid value and a reduced peroxide value. Therefore, the production method of the present invention can provide oils and/or fats with a high degree of refining.

The content of glycidol, 3-chloropropane-1,2-diol, and fatty acid esters thereof in the oils and/or fats and the acid value and the peroxide value of the oils and/or fats may be determined using the methods described in the EXAMPLES section.

<Determination of the Content of Tocopherols in Refined Oils and/or Fats>

The production method of the present invention provides refined oils and/or fats containing tocopherols at a less reduced concentration.

The content of tocopherols in the oils and/or fats may be determined using the method described in the EXAMPLES section.

<Method of Producing Tocopherols>

As mentioned above, in the first mode, the third distillate fraction obtained after the third distillation step mainly includes tocopherols. In the second mode, the second residual fraction obtained after the second distillation step mainly includes tocopherols. According to the present invention, therefore, high purity tocopherols can be obtained by collecting only the third distillate fraction in the first mode or only the second residual fraction in the second mode.

EXAMPLES

Hereinafter, the present invention will be specifically described with reference to examples, which are not intended to limit the present invention.

<Preparation of Refined Oils and/or Fats>

Refined palm-based oils and/or fats were prepared by the method shown below using palm-based oils and/or fats (with an iodine value of 52, hereinafter also referred to as the "raw palm-based oils and/or fats") as raw material oils and/or fats. The raw palm-based oils and/or fats are a product obtained by subjecting an RBD palm oil to decolorization (decolorization conditions: 0.65% of white earth added to the oil) and then deodorization (deodorization conditions: 245° C. and a degree of vacuum of 5 to 6 Torr). This example is one example in the first mode.

(First Distillation Step)

The raw palm-based oils and/or fats were introduced to the evaporating surface of a short-path evaporator KDL-5 (manufactured by UIC GmbH with an evaporating surface area of 480 cm², a condensing surface area of 650 cm², and a maximum flow rate of 1 L/hr) and subjected to thin film distillation (short-path distillation in this example) under the conditions shown in Table 1. The duration of retention of the raw palm-based oils and/or fats on the evaporating surface of the short-path evaporator (namely, the duration of the thin film distillation) was set in the range of 5 seconds or more and 30 seconds or less.

After the short-path distillation under the conditions shown above, the resulting residual fraction (first residual fraction) and the resulting distillate fraction (first distillate fraction) were collected. In this step, the distillate fraction percentage (the percentage of the distillate fraction in the total amount of the collected residual and distillate fractions) was 11.8%.

(Second Distillation Step)

The first distillate fraction obtained in the first distillation step was introduced to the evaporating surface of a short-path evaporator KDL-5 (manufactured by UIC GmbH with an evaporating surface area of 480 cm², a condensing surface area of 650 cm², and a maximum flow rate of 1 L/hr) and subjected to thin film distillation (short-path distillation in this example) under the conditions shown in Table 1. The duration of retention of the raw palm-based oils and/or fats on the evaporating surface of the short-path evaporator (namely, the duration of the thin film distillation) was set in the range of 5 seconds or more and 30 seconds or less.

After the short-path distillation under the conditions shown above, the resulting residual fraction (second residual fraction) and the resulting distillate fraction (second distillate fraction) were collected. In this step, the distillate fraction percentage was 0.24%.

(Third Distillation Step)

The second residual fraction obtained in the second distillation step was introduced to the evaporating surface of a short-path evaporator KDL-5 (manufactured by UIC GmbH with an evaporating surface area of 480 cm², a condensing surface area of 650 cm², and a maximum flow rate of 1 L/hr) and subjected to thin film distillation (short-path distillation in this example) under the conditions shown in Table 1. The duration of retention of the raw palm-based oils and/or fats on the evaporating surface of the short-path evaporator (namely, the duration of the thin film distillation) was set in the range of 5 seconds or more and 30 seconds or less.

After the short-path distillation under the conditions shown above, the resulting residual fraction (third residual fraction) and the resulting distillate fraction (third distillate fraction) were collected.

TABLE 1

| Conditions for thin film distillation (short-path distillation) | | | |
|---|---|---|---|
| | First distillation step | Second distillation step | Third distillation step |
| Material to be treated | RBD palm oil (Raw palm-based oils and/or fats) | First distillate fraction | Second residual fraction |
| Evaporator temperature (° C.) | 270 | 180 | 190 |
| Degree of vacuum in evaporator (mbar) | $1.8~2.4 \times 10^{-4}$ | $3.7~4.2 \times 10^{-7}$ | $3.7~4.2 \times 10^{-7}$ |
| Flow rate (L/hr) | 4.44 L/h | 1.8 L/h | 1.8 L/h |

(Preparation of Mixed Oil)

Mixed were 4,000 g of the first residual fraction and 8 g of the third distillate fraction to form a mixed oil (corresponding to refiled palm-based oils and/or fats). The mixed oil was subjected to deodorization at 220° C. for 80 minutes to give a deodorized mixed oil (this oils and/or fats also corresponds to refined palm-based oils and/or fats).

<Analysis of Composition>

The composition of each of the samples (the raw palm-based oils and/or fats prior to the short-path distillation, the residual and distillate fractions obtained after each distillation step, and the mixed oil) was analyzed as shown below. Table 2 shows the results.

(Quantification of Total Tocopherols)

The content of total tocopherols (the total amount of tocopherol isomers) in each sample was measured according to Japan Oil Chemists' Society, "Standard Methods for the Analysis of Fats, Oils, and Related Materials, 2.4.10-2003, Tocopherols" (fluorescence detector-high performance liquid chromatography method).

(Quantification of Total Tocotrienols)

The content of total tocotrienols (the total amount of tocotrienol isomers) in each sample was measured according Japan Oil Chemists' Society, "Standard Methods for the Analysis of Fats, Oils, and Related Materials, 2.4.10-2003, Tocopherols" (fluorescence detector-high performance liquid chromatography method).

(Quantification of Diglycerides)

The content of diglycerides in each sample was measured according to AOCS "Official Method Cd 11b-91 Determination of Mono- and Diglycerides by Capillary Gas Chromatography".

(Quantification of True MCPD)

The 3-MCPD-equivalent, total amount of 3-MCPD and fatty acid esters of 3-MCPD in each refined oils and/or fats (the total amount is referred to as "True MCPD") was determined according to the modified German official method (DGF Standard Methods C-III 18(09)).

Specifically, 50 µL of an internal standard material (20 µg/mL 3-MCPD-d5 solution) was added to 100 mg of each refined oils and/or fats, and then 1 mL of a sodium methoxide solution (0.5 mol/L methanol) was added, and the mixture was allowed to react at room temperature so that the esters were decomposed by saponification. Subsequently, 3 mL of a sodium bromide (50%) aqueous solution containing a trace amount of acetic acid and 3 mL of hexane were added to and mixed with the reaction mixture, and then the hexane was removed.

Subsequently, the reaction product was derivatized with 500 µL of a phenylboric acid (12.5%) aqueous solution. The derivatives were extracted with 2 mL of hexane and then measured with a gas chromatograph-mass spectrometer. The ion intensity of 3-MCPD was compared with that of 3-MCPD-d5 as the internal standard using the chromatogram obtained by the gas chromatograph-mass spectrometer measurement, when the free 3-MCPD-equivalent, total amount of 3-MCPD and fatty acid esters of 3-MCPD in the glyceride composition was calculated.

(Quantification of Glycidol)

First, MCPD-FS was quantified by the method shown below.

[Quantification of MCPD-FS]

The 3-MCPD-equivalent, total amount of 3-MCPD, glycidol, and fatty acid esters thereof in each refined oils and/or fats (the total amount is referred to as "MCPD-FS") was determined according to the German official method (DGF Standard Methods C-III 18(09)). Specifically, 50 µL of an internal standard material (20 µg/mL 3-MCPD-d5 solution) was added to 100 mg of each refined oils and/or fats, and then 1 mL of a sodium methoxide solution (0.5 mol/L methanol) was added, and the mixture was allowed to react at room temperature so that the esters were decomposed by saponification. Subsequently, 3 mL of a sodium chloride (20%) aqueous solution containing a trace amount of acetic acid and 3 mL of hexane were added to and mixed with the reaction mixture, and then the hexane was removed. Subsequently, the reaction product was derivatized with 250 µL of a phenylboric acid (25%) aqueous solution. The derivatives were extracted with 2 mL of hexane and then measured with a gas chromatograph-mass spectrometer. The ion intensity of 3-MCPD was compared with that of 3-MCPD-d5 as the internal standard using the chromatogram obtained by the gas chromatograph-mass spectrometer measurement, when the free 3-MCPD-equivalent, total amount of 3-MCPD, glycidol, and fatty acid esters thereof in the oils and/or fats was calculated.

[Calculation of the Amount of Glycidol]

The amount of glycidol (the glycidol-equivalent, total amount of glycidol and fatty acid esters thereof) in each refined oils and/or fats was calculated according to the formula below using the MCPD-FS value and the True MCPD value determined by the methods shown above.

Glycidol amount=(MCPD-FS−True MCPD)×0.67

In the formula, "0.67" is the value obtained by dividing the molecular weight (74.1) of glycidol by the molecular weight (110.54) of 3-MCPD.

TABLE 2

| | Composition analysis | | | | | | |
|---|---|---|---|---|---|---|---|
| | RBD palm oil (Raw palm-based oils and/or fats) | First residual fraction | First distillate fraction | Second residual fraction | Second distillate fraction | Mixed oil | Deodorized mixed oil |
| Total tocopherols (%) | 0.0112 | 0.0035 | 0.069 | 0.0 | 2.51 | 0.0085 | 0.0077 |
| Total tocotrienols (%) | 0.0213 | 0.0010 | 0.170 | 0.0 | 1.10 | 0.0032 | 0.0031 |
| Diglycerides (%) | 11.7000 | 5.8000 | 86.000 | 5.9 | 10.00 | 5.8000 | 5.6000 |
| True MCPD (mg/kg) | 2.9000 | 0.8000 | 18.000 | 0.8 | 0.00 | 0.9000 | 0.9000 |
| Glycidol (mg/kg) | 1.0000 | 0.2000 | 6.850 | 0.2 | 0.00 | 0.2000 | 0.2000 |

As shown in Table 2, the mixed oil and the deodorized mixed oil (each corresponding to refined palm-based oils and/or fats) contained a sufficient amount of tocopherols in spite of their significantly reduced amounts of glycidol, 3-chloropropane-1,2-diol, and fatty acid esters thereof as compared to the raw palm-based oils and/or fats.

<Analysis of Physical Properties>

The physical properties of each of the samples (the raw palm-based oils and/or fats prior to the short-path distillation, the first residual fraction, and the mixed oil) were analyzed as shown below. Table 3 shows the results.

(Acid Value)

The acid value of each sample was measured according to Japan Oil Chemists' Society, "Standard Methods for the Analysis of Fats, Oils, and Related Materials, 2.3.1-2013 Acid Value".

(Peroxide Value (POV))

The peroxide value of each sample was measured according to Japan Oil Chemists' Society, "Standard Methods for the Analysis of Fats, Oils, and Related Materials, 2.5.2.1-2013 Peroxide Value".

(CDM Value)

The CDM value of each sample was measured according to Japan Oil Chemists' Society, "Standard Methods for the Analysis of Fats, Oils, and Related Materials, 2.5.1.2-2013 CDM Test". The analysis was carried out using a constant temperature bath at a temperature of 120° C.

(60° C. Storage Test)

To a light-tight closed container was added 500 g of each sample and then stored at 60° C. for 2 weeks (in a dark place). After the storage, the flavor, acid value, peroxide value, and chromaticity of each sample were measured. The acid value and the peroxide value were measured by the methods described above.

[Flavor Evaluation]

The flavor of each sample was evaluated using the rating scale below with reference to the flavor of RBD palm oil as a standard.

3: The sample has the same flavor as that of RBD palm oil.
2+: The sample appears to have a flavor slightly deteriorated as compared to that of RBD palm oil.
2: The sample appears to have a flavor deteriorated as compared to that of RBD palm oil.
1: The sample is severely deteriorated and unacceptable as edible oil.

[Chromaticity]

The chromaticity of each sample was measured according to Japan Oil Chemists' Society, "Standard Methods for the Analysis of Fats, Oils, and Related Materials, 2.2.1.1-2013 Color (Lovibond method)". In the analysis, the liquid layer in the glass cell had a length of 133.4 mm.

TABLE 3

| | | Analysis of physical properties | | | |
|---|---|---|---|---|---|
| | | Raw palm-based oils and/or fats | First residual fraction | Mixed oil | Deodorized mixed oil |
| Acid value | | 0.05 | 0.03 | 0.03 | 0.03 |
| Peroxide value | | 0.5 | 1.8 | 2.2 | 0.0 |
| CDM value | | 13.08 | 6.28 | 9.33 | 12.34 |
| 60° C. Storage test | Flavor | 3 | 2 | 2+ | 3 |
| | Peroxide value | 2.8 | 4.1 | 4.2 | 2.2 |
| | Acid value | 0.05 | 0.04 | 0.04 | 0.04 |
| | Chromaticity | 12Y/1.2R | 14Y/1.4R | 14Y/1.4R | 14Y/1.4R |

As shown in Table 3, the mixed oil and the deodorized mixed oil (each corresponding to refined oils and/or fats (refined palm oils and/or fats)) had a similar level of stability against oxidation to that of the raw material oils and/or fats (raw palm-based oils and/or fats).

The invention claimed is:

1. A method of producing refined oils and/or fats, comprising:
    a type 1 distillation step that comprises subjecting raw material oils and/or fats to thin film distillation under a type 1 condition;
    a type 2 distillation step that comprises subjecting a type 1 distillate fraction obtained after the type 1 distillation step to thin film distillation under a type 2 condition;
    a type 3 distillation step that comprises subjecting a type 2 residual fraction obtained after the type 2 distillation step to thin film distillation under a type 3 condition; and
    a mixing step that comprises mixing a type 1 residual fraction obtained after the type 1 distillation step and a type 3 distillate fraction obtained after the type 3 distillation step to obtain a mixed oil,
    the type 1 condition including a temperature of 250° C. or more and 290° C. or less and a degree of vacuum of 0.1 Pa or less,
    the type 2 condition and the type 3 condition each including a temperature lower than that in the type 1 condition and a degree of vacuum of 0.1 Pa or less,
    the temperature in the type 2 condition being 5° C. or more and 15° C. or less lower than that in the type 3 condition.

2. A method of producing refined oils and/or fats, comprising:
    a type 1 distillation step that comprises subjecting raw material oils and/or fats to thin film distillation under a type 1 condition;
    a type 3 distillation step that comprises subjecting a type 1 distillate fraction obtained after the type 1 distillation step to thin film distillation under a type 3 condition;
    a type 2 distillation step that comprises subjecting a type 3 distillate fraction obtained after the type 3 distillation step to thin film distillation under a type 2 condition; and
    a mixing step that comprises mixing a type 1 residual fraction obtained after the type 1 distillation step and a type 2 residual fraction obtained after the type 2 distillation step to obtain a mixed oil, the type 1 condition including a temperature of 250° C. or more and 290° C. or less and a degree of vacuum of 0.1 Pa or less, the type 2 condition and the type 3 condition each including a temperature lower than that in the type 1 condition and a degree of vacuum of 0.1 Pa or less, the temperature in the type 2 condition being 5° C. or more and 15° C. or less lower than that in the type 3 condition.

3. The method according to claim 1, wherein the temperature in the type 2 condition is 175° C. or more and 185° C. or less.

4. The method according to claim 1, wherein the temperature in the type 3 condition is 185° C. or more and 195° C. or less.

5. The method according to claim 1, wherein the raw material oils and/or fats are oils and/or fats having undergone at least a deodorization step.

6. The method according to claim 1, wherein the raw material oils and/or fats are palm-based oils and/or fats.

7. The method according to claim 1, wherein the thin film distillation is short-path distillation.

8. A method of producing tocopherols, comprising:

a type 1 distillation step that comprises subjecting raw material oils and/or fats to thin film distillation under a type 1 condition;

a type 2 distillation step that comprises subjecting a type 1 distillate fraction obtained after the type 1 distillation step to thin film distillation under a type 2 condition;

a type 3 distillation step that comprises subjecting a type 2 residual fraction obtained after the type 2 distillation step to thin film distillation under a type 3 condition; and a collecting step that comprises collecting a type 3 distillate fraction obtained after the type 3 distillation step, the type 1 condition including a temperature of 250° C. or more and 290° C. or less and a degree of vacuum of 0.1 Pa or less, the type 2 condition and the type 3 condition each including a temperature lower than that in the type 1 condition and a degree of vacuum of 0.1 Pa or less, the temperature in the type 2 condition being 5° C. or more and 15° C. or less lower than that in the type 3 condition.

9. A method of producing tocopherols, comprising:

a type 1 distillation step that comprises subjecting raw material oils and/or fats to thin film distillation under a type 1 condition;

a type 3 distillation step that comprises subjecting a type 1 distillate fraction obtained after the type 1 distillation step to thin film distillation under a type 3 condition;

a type 2 distillation step that comprises subjecting a type 3 distillate fraction obtained after the type 3 distillation step to thin film distillation under a type 2 condition; and a collecting step that comprises collecting a type 2 residual fraction obtained after the type 2 distillation step, the type 1 condition including a temperature of 250° C. or more and 290° C. or less and a degree of vacuum of 0.1 Pa or less, the type 2 condition and the type 3 condition each including a temperature lower than that in the type 1 condition and a degree of vacuum of 0.1 Pa or less, the temperature in the type 2 condition being 5° C. or more and 15° C. or less lower than that in the type 3 condition.

10. The method according to claim 2, wherein the temperature in the type 2 condition is 175° C. or more and 185° C. or less.

11. The method according to claim 2, wherein the temperature in the type 3 condition is 185° C. or more and 195° C. or less.

12. The method according to claim 2, wherein the raw material oils and/or fats are oils and/or fats having undergone at least a deodorization step.

13. The method according to claim 2, wherein the raw material oils and/or fats are palm-based oils and/or fats.

14. The method according to claim 2, wherein the thin film distillation is short-path distillation.

15. The method according to claim 1, wherein the raw material oils and/or fats comprise raw palm-based oils and/or fats.

16. The method according to claim 15, wherein the raw palm-based oils and/or fats comprise refined bleached deodorized palm oil.

17. The method according to claim 16, wherein:

the type 1 condition includes a temperature of 270° C. and a degree of vacuum of $1.8\text{-}2.4\times10^{-2}$ Pa;

the type 2 condition includes a temperature of 180° C. and a degree of vacuum of $3.7\text{-}4.2\times10^{-5}$ Pa; and the type 3 condition includes a temperature of 190° C. and a degree of vacuum of $3.7\text{-}4.2\times10^{-5}$ Pa.

* * * * *